United States Patent [19]

Henning et al.

[11] Patent Number: 4,620,012
[45] Date of Patent: Oct. 28, 1986

[54] SPIROCYCLIC AMINOACID DERIVATIVES, PROCESSES FOR THEIR PREPARATION, AGENTS CONTAINING THEM AND THEIR USE AND NEW SPIROCYCLIC AMINOACIDS AS INTERMEDIATES AND PROCESSES FOR THEIR PREPARATION

[75] Inventors: Rainer Henning, Frankfurt am Main; Hansjörg Urbach, Kronberg; Volker Teetz, Hofheim am Taunus; Reinhard Becker, Wiesbaden, all of Fed. Rep. of Germany

[73] Assignee: Hoechst Aktiengesellschaft, Fed. Rep. of Germany

[21] Appl. No.: 569,758

[22] Filed: Jan. 10, 1984

[30] Foreign Application Priority Data

Jan. 12, 1983 [DE] Fed. Rep. of Germany ....... 3300774

[51] Int. Cl.⁴ .................... C07C 103/52; A61K 37/02
[52] U.S. Cl. .................................................. 548/411
[58] Field of Search ...................... 548/411; 260/112.5

[56] References Cited

FOREIGN PATENT DOCUMENTS 0012401 6/1980 European Pat. Off. .
0050800 5/1982 European Pat. Off. .
0090341 10/1983 European Pat. Off. .

*Primary Examiner*—Morton Foelak
*Assistant Examiner*—M. L. Moore
*Attorney, Agent, or Firm*—Finnegan, Henderson, Farabow, Garrett & Dunner

[57] ABSTRACT

The invention relates to new spirocyclic aminoacid derivatives of the formula I

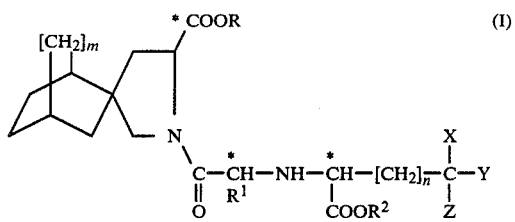

in which
  m denotes 1 or 2, n denotes 0 or 1, R denotes hydrogen, alkyl or aralkyl, $R^1$ denotes hydrogen or alkyl which can be optionally substituted by amino, acylamino or benzoylamino, alkenyl, cycloalkyl, cycloalkenyl, cycloalkylalkyl, aryl or partially hydrogenated aryl, each of which can be substituted by alkyl, alkoxy or halogen, arylalkyl or aroylalkyl, both of which can be substituted as defined above in the aryl radical, an S- or O- and/or N-heterocyclic radical or a side chain of an α-aminoacid, $R^2$ denotes hydrogen, alkyl, alkenyl or aralkyl, Y denotes hydrogen or hydroxyl, Z denotes hydrogen, or Y and Z together denote oxygen and X denotes alkyl, alkenyl, cycloalkyl, aryl, which can be monosubstituted, disubstituted or trisubstituted by alkyl, alkoxy, hydroxyl, halogen, nitro, amino, alkylamino, dialkylamino and/or methylenedioxy, or 3-indolyl, processes for their preparation, agents containing them and their use and new spirocyclic aminoacids as intermediates and a process for their preparation.

8 Claims, No Drawings

SPIROCYCLIC AMINOACID DERIVATIVES, PROCESSES FOR THEIR PREPARATION, AGENTS CONTAINING THEM AND THEIR USE AND NEW SPIROCYCLIC AMINOACIDS AS INTERMEDIATES AND PROCESSES FOR THEIR PREPARATION

The invention relates to new spirocyclic amino-acid derivatives of the formula I

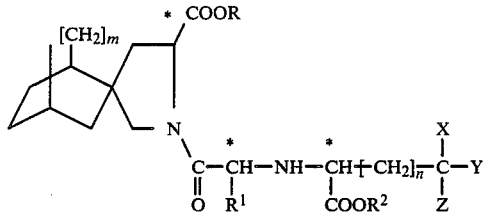

in which
m denotes 1 or 2,
n denotes 0 or 1,
R denotes hydrogen, ($C_1$ to $C_6$)-alkyl or aralkyl having 7 to 9 carbon atoms,
$R^1$ denotes hydrogen or ($C_1$ to $C_6$)-alkyl which can optionally be substituted by amino, ($C_1$ to $C_6$)-acylamino, in particular ($C_1$ to $C_6$)-alkanoylamino or BOC-NH, or benzoylamino, ($C_2$ to $C_6$)-alkenyl, ($C_5$ to $C_9$)-cycloalkyl, ($C_5$ to $C_9$)-cycloalkenyl, ($C_5$ to $C_7$)-cycloalkyl-($C_1$ to $C_4$)-alkyl, ($C_6$ to $C_{12}$)-aryl or partially hydrogenated ($C_6$ to $C_{12}$)-aryl, each of which can be substituted by ($C_1$ to $C_4$)-alkyl, ($C_1$ or $C_2$)-alkoxy or halogen, ($C_6$ to $C_{12}$)-aryl-($C_1$ to $C_4$)-alkyl or ($C_7$ to $C_{13}$)-aroyl-($C_1$ to $C_2$)-alkyl, both of which can be substituted in the aryl radical as defined above, a monocyclic or bicyclic heterocyclic radical having 5 to 7 or 8 to 10 ring atoms respectively, 1 to 2 ring atoms representing sulfur of oxygen atoms and/or 1 to 4 ring atoms representing nitrogen atoms, or an optionally protected side chain of a naturally occurring α-aminoacid,
$R^2$ denotes hydrogen, ($C_1$ to $C_6$)-alkyl, ($C_2$ to $C_6$)-alkenyl or ($C_6$ to $C_{12}$)-aryl-($C_1$ to $C_4$)-alkyl,
Y denotes hydrogen or hydroxyl,
Z denotes hydrogen or
Y and Z together denote oxygen and
X denotes ($C_1$ to $C_6$)-alkyl, ($C_2$ to $C_6$)-alkenyl, ($C_5$ to $C_9$)-cycloalkyl, ($C_6$ to $C_{12}$)-aryl which can be monosubstituted, disubstituted or trisubstituted by ($C_1$ to $C_4$)-alkyl, ($C_1$ to $C_4$)-alkoxy, hydroxyl, halogen, nitro, amino, ($C_1$ to $C_4$)-alkylamino, di-($C_1$–$C_4$)-alkylamino and/or methylenedioxy, or 3-indolyl, and their physiologically acceptable salts.

When $R^1$ represents a protected side chain of a naturally occurring α-aminoacid, such as, for example, protected Ser, Thr, Asp, Asn, Glu, Gln, Arg, Lys, Hyl, Cys, Orn, Cit, Tyr, Trp, His or Hyp, the preferred protective groups are the groups customary in peptide chemistry (compare Houben-Weyl, Vol. XV/1 and XV/2). In the case where $R^1$ denotes the protected side chain of lysine, the known amino protective groups, but particularly ($C_1$–$C_6$)-alkanoyl, are preferred. In the case where $R^1$ denotes the protected side chain of tyrosine, the ether protective group on the oxygen, especially ($C_1$–$C_6$)-alkyl, is preferred; particularly preferred protective groups are methyl and ethyl.

Particularly suitable salts are alkali metal and alkaline earth metal salts, salts with physiologically tolerated amines and salts with inorganic or organic acids, such as, for example, HCl, HBr, $H_2SO_4$, maleic acid and fumaric acid.

In this context and in the following text, aryl is preferably understood to be optionally substituted phenyl or naphthyl. Aroyl is especially understood to be benzoyl. Alkyl can be straight-chain or branched.

A monocyclic or bicyclic heterocyclic radical having 5 to 7 or 8 to 10 ring atoms respectively, 1 to 2 ring atoms representing sulfur or oxygen atoms and/or 1 to 4 ring atoms representing nitrogen atoms, is understood to be, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completely hydrogenated.

Compounds of the formula I have chiral carbon atoms. The invention relates to both the R and the S configurations at all centers of asymmetry. Thus the compounds of the formula I can exist as optical isomers, as diastereomers, as racemates or as mixtures of these. However, compounds of the formula I in which the carbon atoms labeled with an asterisk (*) have the S configuration are preferred. However, when (—CO—$CHR^1$—NH—) is Cys, the R configuration at this center is preferred.

Particularly preferred compounds of the formula I are those in which
m denotes 1 or 2,
n denotes 1,
R denotes hydrogen or alkyl having 1 to 4 carbon atoms,
$R_1$ denotes hydrogen, ($C_1$ to $C_3$)-alkyl, ($C_2$ or $C_3$)-alkenyl, benzyl, 4-methoxybenzyl, 4-ethoxybenzyl, phenethyl, 4-aminobutyl or benzoylmethyl,
$R_2$ denotes hydrogen, ($C_1$ to $C_4$)-alkyl or benzyl and
X denotes cyclohexyl or phenyl which can be monosubstituted or disubstituted, or in the case of methoxy, trisubstituted, by ($C_1$ or $C_2$)-alkyl, ($C_1$ or $C_2$)-alkoxy, hydroxyl, fluorine, chlorine, bromine, amino, ($C_1$ to $C_4$)-alkylamino, di-($C_1$ to $C_4$)-alkylamino, nitro and/or methylenedioxy, especially those compounds of the formula I in which m denotes 1 or 2, n denotes 1, R denotes hydrogen, $R^1$ denotes methyl, 4-methoxybenzyl or 4-ethoxybenzyl, $R^2$ denotes hydrogen or ethyl, and the chiral carbon atoms which are identified with an asterisk (*) have the S configuration.

The —COOR group in the tricyclic aminoacid radical can be located exo or endo with respect to the bicyclic radical; thus the preferred compounds of the invention contain one of the two partial structures of the formulae Ia and Ib

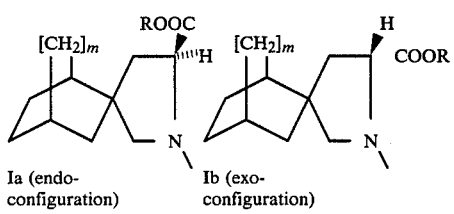

Ia (endo-configuration)   Ib (exo-configuration)

and their mirror images.

The invention also relates to processes for the preparation of compounds of the formula I. One process variant comprises reacting, by methods of amide formation known in peptide chemistry, a compound of the formula II

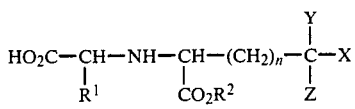   (II)

in which n, $R^1$, $R^2$, X, Y and Z have the same meaning as in formula I, with a compound of the formula III

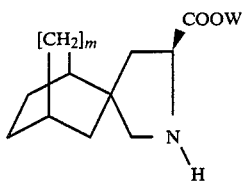   (III)

in which W denotes hydrogen or a radical which can be split off with acid or by hydrogenolysis, especially a tert.-butyl radical or a benzyl radical, and, where appropriate, subsequently splitting off, by acid treatment or hydrogenation, the radical W and, where appropriate, by additional acid or base treatment also splitting off the radical $R^2$, the free carboxylic acids being obtained in each case.

Further synthetic processes for the preparation of the compounds of the formula I in which Y and Z together denote oxygen comprise reacting, in a known manner in a Michael reaction (Organikum, 6th edition, page 492, 1967), a compound of the formula IV

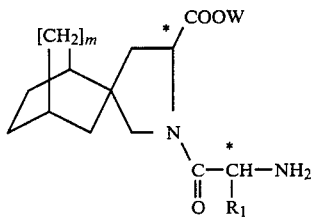   (IV)

in which m and $R^1$ have the same meaning as in formula I and W has the same meaning as in formula III, with a compound of the formula V

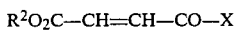   (V)

in which $R^2$ and X have the same meanings as in formula I, and, where appropriate, splitting off the radical W and/or the radical $R^2$, as described above, or comprise reacting, in a known manner in a Mannich reaction (Bull. Soc. Chim. France 1973, page 625), a compound of the abovementioned formula IV with a compound of the general formula VI, in which $R^2$ has the same meaning as in formula I, and with a compound of the general formula VII

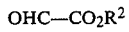   (VI)

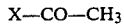   (VII)

in which X has the same meaning as in formula I, and then, where appropriate, splitting off the radical W and/or the radical $R^2$ as described above, with the formation of the free carboxyl groups.

Furthermore, compounds of the formula I with Y and Z each being hydrogen can also be prepared in a manner such that a compound of the abovementioned formula IV is reacted in accordance with the procedure described in J. Amer. Chem. Soc. 93, 2897 (1971) with a compound of the formula VIII

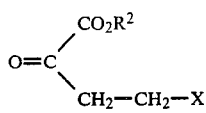   (VIII)

in which $R^2$ and X have the same meanings as in formula I, the resulting Schiff's bases are reduced and then, where appropriate, the radical W and/or the radical $R^2$ are split off as described above, with the formation of the free carboxyl groups. The reduction of the Schiff's bases can be carried out electrolytically or with reducing agents, such as, for example, sodium borohydride or sodium cyanoborohydride.

Compounds of the formula I with Y being hydroxyl and Z being hydrogen can also be obtained, for example, by reduction of a compound I, with Y and Z together being oxygen, obtained in accordance with the above procedures. This reduction can be carried out with a reducing agent, such as sodium borohydride and other complex boranates or, for example, borane-amine complexes.

Compounds of the formula I in which R represents hydrogen can, where appropriate, be converted by methods which are known per se into their esters of the formula I in which R denotes ($C_1$ to $C_6$)-alkyl or ($C_7$ to $C_9$)-aralkyl.

The invention also relates to compounds of the formula III

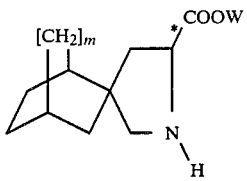   (III)

in which m denotes 1 or 2 and W denotes hydrogen or a radical which can be split off with acid or by hydrogenolysis, such as tert.-butyl or benzyl. These compounds are used in accordance with the invention as starting materials for the synthesis of compounds of the formula I and can be prepared according to the invention by hydrolyzing a compound of the formula XIV

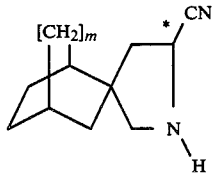   (XIV)

with a mineral acid, such as hydrochloric acid or hydrobromic acid, or with a strong base, such as an alkali metal hydroxide, at 20° C. to 150° C., particularly at 60° to 120° C., preferably in water as the solvent, and esterifying the resulting aminoacids (III/W=hydrogen), where appropriate, by customary methods of aminoacid chemistry. The aminoacids (III/W=hydrogen) or the resulting esters (III/W≠hydrogen) can be separated, for example by chromatography or fractional crystallization of suitable salts, into stereoisomers.

The tricyclic nitriles of the formula XIV can be prepared according to the invention by reacting a bicyclic nitrile of the formula (IX)

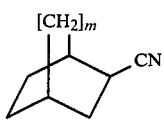 (IX)

in which m is 1 or 2, in the presence of a strong base, such as an alkali metal amide, preferably lithium diisopropylamide, lithium diethylamide or lithium hexamethyldisilazide, with a compound of the formula (X)

$$X-CH_2-CH{\overset{\displaystyle OR^3}{\underset{\displaystyle OR^3}{}}} \quad (X)$$

in which X denotes halogen, particularly chlorine, bromine or iodine, and $R^3$ denotes identical or different ($C_1$ to $C_4$)-alkyl groups, or both radicals $R^3$ together form an ethylene or propylene bridge, in an aprotic solvent, such as tetrahydrofuran, at $-100°$ C. to $+50°$ C., preferably $-80°$ C. to $0°$ C., to give a compound of the formula (XI)

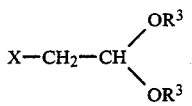 (XI)

in which m and $R^3$ have the above meanings, reducing the latter with a suitable reducing agent, such as, for example, lithium aluminum hydride in an aprotic solvent, preferably diethyl ether or tetrahydrofuran at $0°$ C. to $80°$ C., preferably at $20°$ C. to $60°$ C., or in an alcoholic solvent, preferably ethanol or n-butanol at $0°$ C. to $120°$ C., preferably at $20°$ C. to $80°$ C., or by catalytic hydrogenation in an alcoholic solvent with the addition of ammonia at $0°$ C. to $80°$ C., preferably $20°$ C. to $50°$ C., in the presence of a noble metal or Ni catalyst, preferably Raney nickel or rhodium on aluminum oxide, to give a compound of the formula (XII)

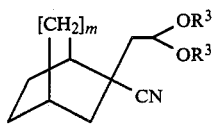 (XII)

in which m and $R^3$ have the above meanings, cyclizing the latter by treatment with a mineral acid, preferably hydrochloric acid, in water at $20°$ C. to $140°$ C., preferably $40°$ C. to $100°$ C., to give a compound of the formula (XIII)

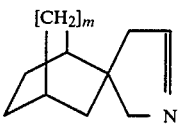 (XIII)

in which m is 1 or 2, and which is produced as a mixture with its trimer, and converting this compound by reaction with an alkali metal cyanide, preferably sodium or potassium cyanide, in water, with the addition of a mineral acid, preferably hydrochloric acid or sulfuric acid, at $0°$ C. to $60°$ C., preferably at $10°$ C. to $40°$ C., into the nitrile of the formula (XIV).

The nitriles of the formula IX are known.

The compounds of the formula II with n=1, Y and Z=hydrogen, $R^1$=methyl and $R^2$=methyl or ethyl and X=phenyl which are used as starting materials for the preparation of the compounds of the formula I are known (European Patent Application No. 37,231). The compounds of the formula II can be prepared by a variety of procedures. One synthesis variant starts from a ketone of the abovementioned formula VII, which is reacted, by known procedures in a Mannich reaction, with a compound of the abovementioned formula VI, together with aminoacid esters of the formula XV

 (XV)

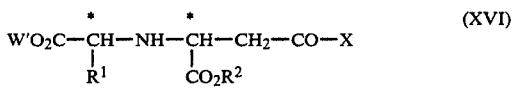 (XVI)

in which $R^1$ has the abovementioned meaning and W' denotes a radical which can be split off by hydrogenolysis or with acid, in particular a benzyl or a tert.-butyl radical, to give a compound of the formula XVI, in which $R^1$, $R^2$, X and W' have the abovementioned meanings, with the proviso that, when W' denotes a radical which can be split off by hydrogenolysis, in particular benzyl, $R^2$ must not have the meaning of W'. If the radical W' is split off by hydrogenolysis with the aid of, for example, palladium, when 3 mole equivalents of hydrogen have been taken up, compounds of the formula II with X and Z=hydrogen are obtained. If the uptake of hydrogen is stopped at 1 mole equivalent, compounds of the formula II with n=1 and Y and Z together=oxygen are obtained, and these are also obtained if the radical W' in formula XVI is split off with acids, such as, for example, trifluoroacetic acid or hydrochloric acid, in an inert organic solvent, such as, for example, dioxane.

Compounds of the formula XVI are also accessible by known procedures by Michael addition reactions of a compound of the abovementioned formula V with a compound of the abovementioned formula XV. This process is suitable preferably for the preparation of those compounds of the formula XVI in which $R^1$ denotes methyl, $R^2$ denotes ethyl and X denotes aryl.

The compounds of the formula XVI are produced as mixtures of diastereomers. Preferred diastereomers of the formula XVI are those in which the chiral carbon atoms marked with an asterisk each have the S configuration. These can, for example, be resolved by crystallization or by chromtography, for example on silica gel.

The configurations of the chiral carbon atoms are maintained when the radical W' is subsequently split off.

The compounds of the abovementioned formula IV used as starting materials for the preparation of the compounds of the formula I are obtained from the compounds of the abovementioned formula III by reaction, by knownw procedures, with a N-protected 2-aminocarboxylic acid of the formula XVII

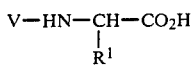 (XVII)

in which V is a protective group and $R^1$ has the abovementioned meaning. An example of a suitable protective group V, which is split off again after reaction is complete, is tert.-butoxycarbonyl.

The reaction of a compound of the formula II with a compound of the formula III for the preparation of a compound of the formula I is effected in accordance with a condensation reaction known in peptide chemistry, dicyclohexylcarbodiimide and 1-hydroxybenzotriazole, for example, being added as the condensing agent. Trifluoroacetic acid or hydrogen chloride are preferably employed as the acids when the radical W is subsequently split off by acids.

The compounds of the formula III obtained in accordance with the procedure described above are produced as a mixture and can be separated from one another, for example, by recrystallization or by chromatography.

The compounds of the formula III are obtained as racemic mixtures and can be employed as such in the synthesis described above. However, they can also be employed as the pure enantiomers after separating the racemates into the optical antipodes by customary methods, for example via salt formation with optically active bases or acids.

If the compounds of the formula I are obtained as racemates, these can also be resolved into their enantiomers by the customary methods, such as, for example, via salt formation with optically active bases or acids, or are separated by chromatography.

When R is hydrogen, the compounds of the formula I according to the invention exist as internal salts. Since they are amphoteric compounds, they can form salts with acids or bases. These salts are prepared in a customary manner by reaction with one equivalent of acid or base.

The compounds of the formula I and their salts have a long-lasting and powerful hypotensive effect. They are strong inhibitors of the angiotensin converting enzyme (ACE inhibitors). They can be employed for the control of high blood pressure of various etiologies. It is also possible to combine them with other compounds having hypotensive, vasodilator or diuretic activity. Typical representatives of these classes of active compounds are described, for example, in Erhardt-Ruschig, Arzneimittel ("Drugs") 2nd edition, Weimheim, 1972. They can be administered intravenously, subcutaneously or orally.

The dosage on oral administration is 0.01–7 mg/kg/day, in particular 0.07–0.5 mg/kg/day. This can also be increased in severe cases, since no toxic properties have hitherto been observed. It is also possible to decrease the dose and this is particularly appropriate when diuretics are administered concurrently.

The compounds according to the invention can be administered orally or parenterally in appropriate pharmaceutical formulations. For a form for oral use, the active compounds are mixed with the additives customary for this purpose, such as vehicles, stabilizers or inert diluents, and converted by conventional methods into suitable forms for administration, such as tablets, coated tablets, hard capsules, aqueous, alcoholic or oily suspensions or aqueous, alcoholic or oily solutions. Examples of inert vehicles which can be used are gum arabic, magnesium carbonate, potassium phosphate, lactose, glucose or starch, especially corn starch. In this context, the formulation can be as either dry or moist granules. Examples of suitable oily vehicles or solvents are vegetable and animal oils, such as sunflower oil and codliver oil.

For subcutaneous or intravenous administration, the active compounds or their physiologically tolerated salts are converted into a solution, suspension or emulsion, if desired with the substances customary for this purpose, such as solubilizers, emulsifiers or other auxiliaries. Examples of suitable solvents for the new active compounds and the corresponding physiologically tolerated salts are: water, physiological sodium chloride solutions or alcohols, for example ethanol, propanediol or glycerol, but also sugar solutions, such as glucose or mannitol solutions, as well as a mixture of the various solvents mentioned.

The extremely strong effect of the compounds according to formula I is demonstrated by the pharmacological data in the table below: Intraduodenal administration to the anesthetized rat, 50% inhibition of the pressor reaction induced by 310 ng of angiotensin I 30 min after administration at the dose ... —$ED_{50}$:

TABLE (The compounds listed have the S configuration at the carbon atoms indicated by an asterisk):

| m | n | X | Y | Z | $R^1$ | $R^2$ | R | Configuration of the COOR group | ED ($\mu$g/kg) |
|---|---|---|---|---|---|---|---|---|---|
| 2 | 1 | $C_6H_5$ | H | H | $CH_3$ | $C_2H_5$ | H | exo | 50 |
| 2 | 1 | $C_6H_5$ | H | H | $CH_3$ | $C_2H_5$ | H | endo | 500 |
| 2 | 1 | $C_6H_5$ | H | H | $CH_3$ | H | H | exo | 200 |
| 2 | 1 | $C_6H_5$ | H | H | $CH_3$ | H | H | endo | 850 |
| 2 | 1 | $C_6H_5$ | O | | $CH_3$ | $C_2H_5$ | H | exo | 80 |
| 2 | 1 | $C_6H_5$ | O | | $CH_3$ | $C_2H_5$ | H | endo | 650 |
| 1 | 1 | $C_6H_5$ | H | H | $CH_3$ | $C_2H_5$ | H | exo/endo | 80 |
| 1 | 1 | $C_6H_5$ | H | H | $CH_3$ | H | H | exo/endo | 240 |
| 1 | 1 | $C_6H_5$ | O | | $CH_3$ | $C_2H_5$ | H | exo/endo | 140 |

The symbols n, m, X, Y, Z, R, $R^1$ and $R^2$ relate to the compounds of the formula I.

The examples which follow serve to illustrate the invention without restricting it to the compounds which are mentioned as representative.

EXAMPLE 1

5'-Cyanospiro[bicyclo[2.2.2]octane-2,3'-pyrrolidine]

(a)

2-Cyano-2-(1,3-dioxolan-2-yl)methylbicyclo[2.2.2]octane 84 ml of diisopropylamine are dissolved in 300 ml of absolute tetrahydrofuran. 39.9 ml of n-butyllithium (1.5 molar in hexane) are added at −20° C. under dry argon. After 30 minutes at room temperature, the mixture is cooled down to −78° C. and 8.1 g of 2-cyanobicyclo[2.2.2]octane in 30 ml of absolute tetrahydrofuran are stirred in, and, after 30 minutes at 0° C., the mixture is again cooled down to −78° C. and 10 g of 2- bromomethyl-1,3-dioxolane in 30 ml of tetrahydrofuran are added dropwise. The mixture is stirred for a further 45 minutes at −78° C., warmed up to room temperature and evaporated, and the residue is taken up in 2N acetic acid and ether, washed three times with water and dried over sodium sulfate and the solvent is removed. The crude product is chromatographed on silica gel with ethyl acetate/cyclohexane (1:6) as the mobile phase. 7.9 g of the title compound are obtained as a colorless oil.

$^1$H-NMR data (CDCl$_3$): 5.02+4.95 (2t, J=6 Hz, 1H); 4.1–3.7 (m, 4H); 1.95 (d, J=6 Hz, 2H); 2.2–1.3 (m, 12H) ppm.

(b) 2-Aminomethyl-2-(1,3-dioxolan-2-yl)methylbicyclo[2.2.2]octane 3.7 g of lithium aluminum hydride are suspended in 60 ml of dry ether; 7.4 g of 2-cyano-2-(1,3-dioxolan-2-yl)methylbicyclo[2.2.2]octane, dissolved in 80 ml of dry ether, are added dropwise so that gentle boiling is maintained. The mixture is then boiled under reflux for 2 hours, then cooled in ice and, in sequence, 2.1 ml of water, 2.1 ml of 1N sodium hydroxide solution and 15 ml of water are added dropwise. The aluminum hydroxide is filtered off with suction and thoroughly washed with ether. 5.5 g of the title compound are obtained as a colorless oil.

$^1$H-NMR data (CDCl$_3$): 4.87 (t, J=6 Hz, 1H); 4.0–3.6 (m, 4H); 2.63 (s, 2H); 2.0–1.0 (m, 14H) ppm.

(c) Spirobicyclo[2.2.2]octane-2,3'-pyrroline-Δ3'

5.5 g of 2-aminomethyl-2-(1,3-dioxolan-2-yl)methylbicyclo[2.2.2]octane are boiled under reflux with 5N hydrochloric acid for 1.5 hours. After extraction with ethyl acetate, the aqueous phase is cooled in ice and 4N potassium hydroxide is added, then it is extracted with ether, the extract is dried with sodium sulfate and the solvent is removed. 3 g of the title compound are obtained as a mixture of the monomer and the trimer (s-triazine derivative).

(d) 5'-Cyanospiro[bicyclo[2.2.2]octane-2,3'-pyrrolidine]

3 g of spiro[bicyclo[2.2.2]octane-2,3'-pyrroline-Δ3'] are dissolved together with 2.25 g of potassium cyanide in 100 ml of water. While cooling in ice, 24 ml of 2N hydrochloric acid are added dropwise and the mixture is stirred at room temperature for 72 hours. After extraction with ethyl acetate, the aqueous phase is made alkaline, with 1N sodium hydroxide solution and extracted with ether and the extract is dried over sodium sulfate. After evaporation, the crude product is chromatographed on silica gel with ethyl acetate/cyclohexane (1:1) as the mobile phase, thus separating the endo and exo isomers.

Endo isomer: 0.83 g, melting point 78°–80° C.
$^1$H-NMR data (CDCl$_3$): 4.0 (t, J=14 Hz, 1H); 2.8 (s, 2H); 2.4 (s, 1H); 2.0 (d, 2H); 1.5 (br. s, 12H).

Exo isomer: 1.5 g, melting point 38°–40° C.
$^1$H-NMR data (CDCl$_3$): 4.02 (X part of an ABX system, 1H); 2.85 (AB system, J=15 Hz, 2H); 2.5–1.0 (m, 15H) ppm.

EXAMPLE 2

Endo-spiro[bicyclo[2.2.2]octane-2,3'-pyrrolidine]-5'-carboxylic acid 0.8 g of endo-5'-cyanospiro[bicyclo[2.2.2]octane-2,3'-pyrrolidine] are boiled under reflux with 20 ml of 5N hydrochloric acid for 5 hours. After evaporation to dryness, the residue is taken up with water, the pH is adjusted to 5.7 by the addition of Amberlite ® IRA 93 (OH$^-$ form), the latter is filtered off and the solution is evaporated. The residue is triturated with methylene chloride/isopropyl ether. 0.9 g of the title compound is obtained as colorless crystals of melting point 236° C.

$^1$H-NMR data (D$_2$O): 4.2 (X part of a ABX system, 1H); 3.2 (s, 2H); 3.2 (s, 2H); 2.5–1.5 (AB part of a ABX system, 2H); 1.5 (br. s, 12H) ppm.

Mass spectrum (m/e): 209 (M$^+$, 0.8%); 165 (13%); 164 (M-COOH, 100%); 87 (14%), 69 (10%).

EXAMPLE 3

Exo-spiro[bicyclo[2.2.2]octane-2,3'-pyrrolidine]-5'-carboxylic acid 1.5 g of exo-5'-cyanospiro[bicyclo[2.2.2]octane-2,3'-pyrrolidine] are reacted with 30 ml of 5N hydrochloric acid by the procedure described in Example 2. 1.68 g of the title compound are obtained as colorless crystals of melting point 242° C.

$^1$H-NMR data (D$_2$O): 4.15 (X part of a ABX system, 1H); 3.2 (AB system, J$_{AB}$=15 Hz, 2H); 2.5–1.7 (AB part of an ABX system, 2H); 1.5 (br. s, 12H) ppm.

Mass spectrum (m/e): 209 (M$^+$, 0.5%); 165 (15%); 164 (M-COOH, 100%); 87 (10%); 69 (8%).

EXAMPLE 4

5'-Cyanospiro[bicyclo[2.2.1]heptane-2,3'-pyrrolidine]

(a) 2-Cyano-2-(1,3-dioxolan-2-yl)methylbicyclo[2.2.1]heptane 7.2 g of norbornane-2-carbonitrile are reacted with 60 mmoles of lithium diisopropylamide (prepared from 8.2 ml of diisopropylamine and 40 ml of n-butyllithium) and with 7 g of 2-bromomethyl-1,3-dioxolane in analogy to Example 1a. After chromatography on silica gel with ethyl acetate/cyclohexane (1:6) as the mobile phase, 8.0 g of the title compound are obtained as an oil.

$^1$H-NMR data (CDCl$_3$): 4.95 (t, J=6 Hz, 1H); 4.0–3.7 (m, 4H); 2.6–2.2 (m, 2H) 2.0–1.2 (m, 10H) ppm.

(b) 2-Aminomethyl-2-(1,3-dioxolan-2-yl)methylbicyclo[2.2.1]heptane 8 g of 2-cyano-2-(1,3-dioxolan-2-yl)methylbicyclo[2.2.1]heptane are reduced with 4.4 g of lithium aluminum hydride in analogy to Example 1b. 6.9 g of a colorless oil are obtained.

$^1$H-NMR data (CDCl$_3$): 4.07 (t, J=6 Hz, 1H); 4.0–3.6 (m, 4H); 2.6 (s, 2H); 2.4–0.7 (m, 14H) ppm.

(c) Spiro[bicyclo[2.2.1]heltane-2,3'-pyrroline-Δ3']

6.9 g of 2-aminomethyl-2-(1,3-dioxolan-2-yl)methylbicyclo[2.2.1]heptane are cyclized with 125 ml of 5N hydrochloric acid by the method of Example 1c. 4.6 g of the title compound are obtained as a mixture of monomer and trimer.

(d) 5'-Cyanospiro[bicyclo[2.2.1]heptane-2,3'-pyrrolidine]

4.6 g of spiro[bicyclo[2.2.1]heptane-2,3'-pyrrolidine-Δ3'] are reacted with 3.85 g of potassium cyanide and 42.8 ml of 2N hydrochloric acid in analogy to the procedure described in Example 1d. 4.4 g of the title compound are obtained as a mixture of isomers.

¹H-NMR data (CDCl₃): 3.98 (X part of an ABX system, 1H); 3.2–1.0 (m, remaining H) ppm.

EXAMPLE 5

Spiro[bicyclo[2.2.1]heptane-2,3'-pyrrolidine]-5'-carboxylic acid 4.4 g of 5'-cyanospiro[bicyclo[2.2.1]heptane-2,3'-pyrrolidine] are hydrolyzed with 120 ml of 5N hydrochloric acid by the procedure described in Example 2. 4.35 g of the title compound are obtained as a colorless powder.

¹H-NMR data (D₂O): 4.3–4.0 (m, 1H); 3.5–3.0 (m, AB system, 2H); 2.5–1.0 (m, 12H) ppm.

EXAMPLE 6

Benzyl endo-spiro[bicyclo[2.2.2]octane-2,3'-pyrrolidine]-5'-carboxylate hydrochloride 0.9 g of endo-spiro[bicyclo[2.2.2]octane-2,3'-pyrrolidine]-5'-carboxylic acid are added to a solution of 0.9 ml of thionyl chloride in 9 ml of benzyl alcohol, prepared at −5° C. After 1 hour at −5° C. and 18 hours at room temperature, the mixture is diluted with water and extracted with ethyl acetate. The ethyl acetate phase is dried over magnesium sulfate and evaporated. The benzyl alcohol is removed under high vacuum. The oily residue is triturated with diisopropyl ether, whereupon the product crystallizes, yield 0.92 g, melting point 139°–142° C.

¹H-NMR data (CDCl₃): 7.3 (s, 5H); 5.25 (s, 2H); 4.52 (t, 1H); 3.4 (s, 2H); 2.5–1.1 (m, 14H) ppm.

EXAMPLE 7

Benzyl exo-spiro[bicyclo[2.2.2]octane-2,3'-pyrrolidine]-5'-carboxylate hydrochloride 1.6 g of exo-spiro[bicyclo[2.2.2]octane-2,3'-pyrrolidine]-5'-carboxylic acid are esterified with 1.6 ml of thionyl chloride and 16 ml of benzyl alcohol in analogy to the procedure described in Example 6, yield 1.68 g, melting point 149°–151° C.

¹H-NMR data (CDCl₃): 7.3 (s, 5H); 5.4–5.0 (AB system, 2H); 4.55 (t, 1H); 3.35 (s, 2H); 2.4–1.2 (m, 14H) ppm.

EXAMPLE 8

Benzyl spiro[bicyclo[2.2.1]heptane-2,3'-pyrrolidine]-5'-carboxylate hydrochloride 4.3 g of spiro[bicyclo[2.2.1]heptane-2,3'-pyrrolidine]-5'-carboxylic acid are esterified with 43 ml of thionyl chloride and 43 ml of benzyl alcohol is analogy to the procedure described in Example 6, yield 6.7 g, ¹H-NMR data (DMSO-d₆): 7.4 (s, 5H); 5.2 (s, 2H); 4.6–4.2 (m, 1H); 3.5–3.0 (m, 2H); 2.4–1.0 (m, 12H) ppm.

Mass spectrum (m/e): 285 (M⁺, 0.1%); 150 (M⁺-CO₂Bzl, 100%).

EXAMPLE 9

Benzyl N-(1-S-carboethoxy-3-phenylpropyl)-S-alanyl-exo-spiro[bicyclo[2.2.2]octane-2,3'-pyrrolidine]-5'-S-carboxylate (diastereomer A9) and benzyl N-(1-S-carboethoxy-3-phenylpropyl)-S-alanyl-exo-spiro[bicyclo[2.2.2]octane-2,3'-pyrrolidine]-5'-R-carboxylate (diastereomer B9)

1.6 g of the benzyl ester from Example 7 are dissolved together with 1.39 g of N-(1S-carboethoxy-3-phenylpropyl S-alanine, 0.59 g of 1-hydroxybenzotriazole and 0.66 ml of N-ethylmorpholine in 15 ml of absolute dimethylformamide. 1.08 g of dicyclohexylcarbodiimide are added and the mixture is stirred at room temperature for 2 hours. The precipitate is filtered off, the filtrate is diluted with ethyl acetate, washed with 10 percent citric acid solution, 1N sodium bicarbonate solution, water and saturated brine, once with each, dried over sodium sulfate and evaporated. Chromatography of the crude product on silica gel with ethyl acetate/cyclohexane (1:2) as the mobile phase provides the two title compounds.

Diastereomer A9: R$_f$ value 0.26 (ethyl acetate/cyclohexane 1:1).

¹H-NMR data (CDCl₃):=7.3 (s, 5H); 7.15 (s, 5H); 5.15 (AB system, 2H); 4.55 (X part of an ABX system, 1H); 4.2 (s, 2H); 3.7–3.1 (m, 3H); 2.9–2.4 (m, 2H); 2.3–1.0 (m, 18H); 1.2 (d+t, 6H) ppm.

Mass spectrum (m/e): 560 (M⁺, 1%), 487 (4%), 355 (3%), 234 (100%).

Diastereomer B9: R$_f$ value 0.20 (ethyl acetate/cyclohexane 1:1).

¹H-NMR data (CDCl₃):=7.3 (s, 5H); 7.15 (s, 5H); 5.2 (s, 2H); 4.6–4.0 (m, 4H); 3.8–3.0 (m, 4H); 2.9–1.0 (m, 18H); 1.2 (d+t, 6H) ppm.

Mass spectrum (m/e): 560 (M⁺, 1%); 487 (4%); 355 (3%), 348 (5%), 234 (100%).

EXAMPLE 10

Benzyl N-(1-S-carboethoxy-3-phenylpropyl)-S-alanyl-endo-spiro[bicyclo[2.2.2]octane-2,3'-pyrrolidine]-5'-(RS)-carboxylate 0.91 g of the benzyl ester from Example 6 are reacted with 0.8 g of N-(1-S-carboethoxy-3-phenylpropyl)-S-alanine, 0.34 g of 1-hydroxybenzotriazole, 0.38 ml of N-ethylmorpholine and 0.62 g of dicyclohexylcarbodiimide by the procedure described in Example 9. Chromatography on silica gel with ethyl acetate/cyclohexane (1:2) as the mobile phase provides 0.96 g of the title compound as a mixture of diastereomers.

¹H-NMR data (CDCl₃):=7.3 (s, 5H); 7.15 (s, 5H); 5.2 (s, 2H); 4.7–4.0 (m, 3H); 3.6–3.0 (m, 4H); 2.9–2.4 (m, 2H); 2.4–1.0 (m, 24H) ppm.

EXAMPLE 11

Benzyl N-(1-S-carboethoxy-3-phenylpropyl)-S-alanylspiro[bicyclo[2.2.1]heptane-2,3'-pyrrolidine]-5'-carboxylate (Diastereomers A11 to C11)

2.0 g of the benzyl ester from Example 8 are reacted with 1.83 g of N-(1-S-carboethoxy-3-phenylpropyl)-S-alanine, 0.78 g of 1-hydroxybenzotriazole, 0.87 ml of N-ethylmorpholine and 1.43 g of dicyclohexylcarbodiimide by the procedure described in Example 9. Three fractions can be separated by chromatography on silica gel with ethyl acetate/cyclohexane as the mobile phase.

Diastereomer A11 (0.28 g) $R_f$ value (ethyl acetate/cyclohexane 1:1) 0.36.

$^1$H-NMR data (CDCl$_3$):=7.3 (s, 5H); 7.15 (s, 5H); 5.2 (AB system, 2H); 4.6–3.9 (m, 4H); 3.6–3.0 (m, 4H); 2.9–2.6 (m, 2H); 2.4–1.0 (m, 22H) ppm.

Diastereomer B11 (0.89 g) $R_f$ value (ethyl acetate/cyclohexane 1:1) 0.32.

$^1$H-NMR data (CDCl$_3$):=7.3 (s, 5H); 7.15 (s, 5H); 5.15 (AB system, 2H); 4.55 (X part of an ABX system, 2H); 4.2 (q, 2H); 4.4–4.0 (m, 1H); 3.7–3.0 (m, 4H); 2.9–2.5 (m, 2H); 2.4–1.0 (m, 22H) ppm.

Diastereomer C11 (0.86 g) $R_f$ value (ethyl acetate/cyclohexane 1:1) 0.29.

$^1$H-NMR data (CDCl$_3$):=7.3 (s, 5H); 7.15 (s, 5H); 5.2 (s, 2H); 4.7–4.0 (m, 4H); 3.8–3.1 (m, 4H); 2.9–2.5 (m, 2H); 2.4–1.0 (m, 22H) ppm.

EXAMPLE 12

N-(1-S-Carboethoxy-3-phenylpropyl)-S-alanyl-exo-spiro[bicyclo[2.2.2]octane-2,3′-pyrrolidine]-5′-S-carboxylic acid hydrochloride 553 mg of the diastereomer A9 from Example 9 are dissolved in 50 ml of ethanol and, after the addition of 0.3 g of Pd/C (10%), are hydrogenated at room temperature and under normal pressure. After filtration, the solution is acidified with 2.5N ethanolic hydrochloric acid and evaporated and the residue is triturated with isopropyl ether.

0.42 g of the title compound, of melting point 128°–130° C. (decomposition), is obtained.

$^1$H-NMR data (DMSO-d$_6$):=7.25 (s, 5H); 4.6–3.0 (m, 7H); 3.0–2.0 (m, 2H); 2.0–1.0 (m, 24H) ppm.

IR data (KBr): 3400, 2930, 2860, 1740, 1650, 1500, 1220, 750, 700 cm$^{-1}$.

EXAMPLE 13

N-(1-S-Carboethoxy-3-phenylpropyl)-S-alanyl-exo-spiro[bicyclo[2.2.2]octane-2,3′-pyrrolidine]-5′-R-carboxylic acid hydrochloride 0.62 g of the diasteromer B9 from Example 9 is hydrogenated by the procedure described in Example 12. 0.41 g of the title compound, of melting point 120° C. (decomposition), is obtained.

$^1$H-NMR data (DMSO-d$_6$):=7.25 (s, 5H); 4.6–3.0 (m, 7H); 3.3–2.0 (m, 2H); 2.0–1.0 (m, 18H); 1.2 (d+t, 6H) ppm.

IR data (KBr): 3400, 2930, 2860, 1740, 1650, 1500, 1225, 750, 700 cm$^{-1}$.

EXAMPLE 14

N-(1-S-Carboethoxy-3-phenylpropyl)-S-alanyl-endo-spiro[bicyclo[2.2.2]octane-2,3′-pyrrolidine]-5′-(RS)-carboxylic acid hydrochloride 0.94 g of the compound from Example 10 is hydrogenated by the process of described in Example 12. 0.7 g of the title compound, of melting point 186°–189° C. (decomposition), is obtained.

$^1$H-NMR data (DMSO-d$_6$):=7.2 (s, 5H); 4.6–3.1 (m, 7H); 3.0–2.0 (m, 2H); 2.0–1.0 (m, 18H); 1.2 (d+t, 6H) ppm.

IR data (KBr): 3420, 2930, 2860, 1740, 1653, 1545, 1500, 1208, 750, 705 cm$^{-1}$.

Mass spectrum (m/e): 470 (M$^+$, 0.01%); 452 (M$^+$-H$_2$O, 16%), 348 (100%), 302 (47%), 263 (16%).

EXAMPLE 15 tert.-Butyl endo-spiro[bicyclo[2.2.2]octane-2,3′-pyrrolidine]-5′-carboxylate hydrochloride 1 ml of concentrated sulfuric acid and 6 g of isobutylene are added to a solution of 1.3 g of the aminoacid from Example 2 in 12 ml of dioxane, cooled to −10° C. After warming up to 25° in an autoclave, the mixture is stirred at this temperature for 20 hours. The mixture is then added to ice-cold 50% strength sodium hydroxide and this mixture is extracted with methylene chloride. The combined organic phases are washed with water and dried with sodium sulfate, the residue is dissolved in ether and gaseous hydrogen chloride is passed in. 0.95 g of the title compound is obtained.

$^1$H-NMR data (DMSO-d$_6$):=4.0–3.5 (m, 1H); 3.2–2.6 (s, 2H); 2.0–1.1 (m, 14H); 1.3 (s, 9H) ppm.

EXAMPLE 16 tert.-Butyl exo-spiro[bicyclo[2.2.2]octane-2,3′-pyrrolidine]-5′-carboxylate hydrochloride Prepared from 0.7 g of the aminoacid from Example 3 by the procedure described in Example 15. 0.6 g of the title compound is obtained.

$^1$H-NMR data (DMSO-d$_6$):=3.9–3.5 (m, 1H); 3.2–2.6 (m, 1H); 2.0–1.1 (m, 14H); 1.3 (s, 9H) ppm.

EXAMPLE 17 tert.-Butyl spiro[bicyclo[2.2.1]heptane-2,3′-pyrrolidine]-5′-carboxylate hydrochloride Prepared from 0.6 g of the aminoacid from Example 5 by the procedure described in Example 15; 0.52 g of the title compound is obtained.

$^1$H-NMR data (DMSO-d$_6$):=3.8–3.5 (m, 1H); 3.2–2.5 (m, 1H); 2.0–1.1 (m, 12H); 1.3 (s, 9H) ppm.

EXAMPLE 18 tert.-Butyl N-(1-S-carboethoxy-3-phenylpropyl)-S-alanylendo-spiro[bicyclo[2.2.2]octane-2,3′-pyrrolidine]-5′-S-carboxylate (Diastereomer A18)

In analogy to the procedure in Example 9, 0.28 g of the title compound is obtained as a colorless oil from 0.58 g of the tert.-butyl ester from Example 15, 0.57 g of N-(1-S-carboethoxy-3-phenylpropyl)-S-alanine, 0.27 g of N-hydroxybenzotriazole and 0.41 g of dicyclohexylcarbodiimide with the addition of 0.23 g of N-ethylmorpholine.

$^1$H-NMR data (CDCl$_3$):=7.1 (s, 5H); 4.5–4.1 (m, 1H); 4.2 (q, J=7 Hz, 2H); 3.9–1.9 (m, 22H); 1.3 (s, 9H); 1.2 (d+t, J=7H$_2$, 6H) ppm.

EXAMPLE 19

N-(1-S-Carboethoxy-3-phenylpropyl)-S-alanyl-endo-spiro[bicyclo[2.2.2]octane-2,3′-pyrrolidine]-5′-S-carboxylic acid hydrochloride 0.28 g of the tert.-butyl ester from Example 18 is dissolved in 1.5 ml of trifluoroacetic acid and stirred at 0° C. for 3 hours. The trifluoroacetic acid is evaporated in vacuo, toluene is added and evaporation is repeated. After filtration through a short column of silica gel with methylene chloride/ethanol (10:1) as the mobile phase, the filtrate is acidified with ethanolic hydrochloric acid and evaporated. After dissolving in a little methylene chloride, the title compound is precipitated with diisopropyl ether. 0.21 g is obtained, which is identical with the compound from Example 12.

EXAMPLE 20

N-(1-S-Carboxy-3-phenylpropyl)-S-alanyl-exo-spiro[bicyclo[2.2.2]octane-2,3'-pyrrolidine]-5'-S-carboxylic acid Two equivalents of potassium hydroxide and a 10% excess of 4N potassium hydroxide solution are added to a solution of 0.25 g of the compound from Example 12 in 2 ml of water. After stirring at 20° to 25° C. for 8 hours, the reaction solution is adjusted to a pH of 4 with 2N hydrochloric acid and evaporated in vacuo. The residue is taken up in ethyl acetate and the precipitated salt is filtered off. The ethyl acetate solution is evaporated, and the residue is triturated with diisopropyl ether and filtered off with suction.

$^1$H-NMR data (DMSO-$d_6$):=7.1 (s, 5H); 4.4–4.0 (m, 1H); 3.9–1.3 (m, 22H); 1.2 (d, 3H) ppm.

EXAMPLE 21

N-(1-S-Carboxy-3-phenylpropyl)-S-alanyl-endo-spiro[bicyclo[2.2.2]octane-2,3'-pyrrolidine]-5'-(RS)-carboxylic acid 0.32 g of the compound from Example 14 are reacted by the process described in Example 20.

$^1$H-NMR data (DMSO-$d_6$):=7.15 (s, 5H); 4.4–3.9 (m, 1H); 3.9–1.3 (m, 22H); 1.2 (d, 3H) ppm.

EXAMPLE 22

N-(1-S-Carboethoxy-3-phenylpropyl)-S-alanyl-spiro[bicyclo[2.2.1]heptane-2,3'-pyrrolidine]-5'-carboxylic acid hydrochloride (Diastereomers A22 to C22)

The diastereomers A11 to C11 from Example 11 are hydrogenated by the procedure described in Example 12. The free carboxylic acids are obtained in each case.

Diastereomer A22 0.17 g, melting point 189° C. (decomposition).

$^1$H-NMR data (DMSO-$d_6$):=7.2 (s, 5H); 4.6–3.0 (m, 7H); 3.0–2.0 (m, 2H); 2.1–1.0 (m, 22H) ppm.

Diastereomer B22 0.79 g, melting point 126° C. (decomposition).

$^1$H-NMR data (DMSO-$d_6$):=7.2 (s, 5H); 4.5–3.1 (m, 7H); 3.1–2.0 (m, 2H); 2.2–1.0 (m, 22H) ppm.

Diastereomer C22 0.63 g, melting point 125° C. (decomposition).

$^1$H-NMR data (DMSO-$d_6$):=7.15 (s, 5H); 4.5–3.1 (m, 7H); 3.0–2.0 (m, 2H); 2.2–1.0 (m, 22H) ppm.

EXAMPLE 23 tert.-Butyl N-(1-S-carboethoxy-3-phenyl-3-oxopropyl)-S-alanyl-exo-spiro[bicyclo[2.2.2]octane-2,3'-pyrrolidine]-5'-S-carboxylate 0.28 g of the tert.-butyl ester from Example 16 is dissolved together with 0.14 g of 1-hydroxybenzotriazole, 0.29 g of N-(1-S-carboethoxy-3-phenyl-3-oxopropyl)-S-alanine, 0.22 g of dicyclohexylcarbodiimide and 0.2 g of N-ethylmorpholine in 3 ml of DMF and the solution is stirred at 20° C. for 3 hours. After dilution with ethyl acetate, the mixture is filtered, and the filtrate is washed twice with water, dried and evaporated. The residue is chromatographed on silica gel with cyclohexane/ethyl acetate (1:1) as the mobile phase; 0.16 g of the title compound is obtained.

$^1$H-NMR data (CDCl$_3$):=8.2–7.1 (m, 5H); 4.7–4.1 (m, 1H); 4.1 (q, 2H); 3.9–1.3 (m, 20H); 1.3 (s, 9H); 1.2 (d+t, 6H) ppm.

EXAMPLE 24 tert.-Butyl N-(1-S-carboethoxy-3-phenyl-3-oxopropyl)-S-alanyl-endo-spiro[bicyclo[2.2.2]octane-2,3'-pyrrolidine]-5'-S-carboxylate 0.28 g of the tert.-butyl ester from Example 15 is reacted by the procedure of Example 23. 0.18 g of the title compound is obtained.

$^1$H-NMR data (CDCl$_3$):=8.2–7.2 (m, 5H); 4.7–4.1 (m, 1H); 4.15 (q, 2H); 3.9–1.2 (m, 20H); 1.3 (s, 9H); 1.2 (d+t, 6H) ppm.

EXAMPLE 25 tert.-Butyl N-(1-S-carboethoxy-3-phenyl-3-oxopropyl)-S-alanyl-spiro[bicyclo[2.2.1]heptane-2,3'-pyrrolidine]-5'-S-carboxylate 0.27 g of the tert.-butyl ester from Example 17 is reacted by procedure of Example 23.

$^1$H-NMR data (CDCl$_3$):=8.1–7.2 (m, 5H); 4.7–4.0 (m, 1H); 4.1 (q, 2H); 3.9–1.2 (m, 18H); 1.3 (s, 9H); 1.2 (d+t, 6H) ppm.

EXAMPLE 26

N-(1-S-Carboethoxy-3-phenyl-3-oxopropyl)-S-alanyl-exospiro[bicyclo[2.2.2]octane-2,3'-pyrrolidine]-5'-S-carboxylic acid hydrochloride 0.12 g of the compound from Example 23 are reacted in analogy to the procedure described in Example 19 to give 0.1 g of the title compound.

$^1$H-NMR data (DMSO-$d_6$):=8.2–7.1 (m, 5H) 4.7–4.1 (m, 1H) 4.1 (q, 2H) 3.9–1.3 (m, 20H) 1.2 (d+t, 6H) ppm.

EXAMPLE 27

N-(1-S-Carboethoxy-3-phenyl-3-oxopropyl)-S-alanyl-endospiro[bicyclo[2.2.2]octane-2,3'-pyrrolidine]-5'-S-carboxylic acid hydrochloride 0.14 g of the compound from Example 24 are reacted in analogy to the procedure described in Example 19 to give 0.11 g of the title compound.

$^1$H-NMR data (DMSO-$d_6$):=8.2–7.1 (m, 5H); 4.7–4.1 (m, 1H); 4.1 (q, 2H); 3.9–1.3 (m, 20H); 1.2 (d+t, 6H) ppm.

EXAMPLE 28

N-(1-S-Carboethoxy-3-phenyl-3-oxopropyl)-S-alanyl-spiro[bicyclo[2.2.1]heptane-2,3'-pyrrolidine]-5'-S-carboxylic acid hydrochloride 0.23 g of the compound from Example 25 are reacted in analogy to the procedure described in Example 19 to give 0.19 g of the title compound.

$^1$H-NMR data (DMSO-$d_6$):=8.2–7.1 (m, 5H); 4.7–4.1 (m, 1H); 4.2 (q, 2H); 3.8–1.2 (m, 18H); 1.2 (d+t, 6H) ppm.

EXAMPLE 29 tert.-Butyl S-alanyl-exo-spiro[bicyclo[2.2.2]octane-2,3'-pyrrolidine]-5'-carboxylate (a) tert.-Butyl N-methylsulfonylethoxycarbonyl-(MSC)-S-alanyl-exo-spiro[bicyclo[2.2.2]octane-2,3'-pyrrolidine]-5'-carboxylate 6.7 g of 1-hydroxybenzotriazole and 16.0 g of tert.-butyl exo-spiro[bicyclo[2.2.2]octane-2,3'-pyrrolidine]-5'-carboxylate are added to a solution of 10 g of MSC-Ala-OH in 50 ml of dimethylformamide. The pH is adjusted to 8.0 with N-ethylmorpholine. The mixture is cooled in an icebath and 10.5 g of dicyclohexylcarbodiimide are added. The mixture is stirred at 20°–25° C. for 15 hours. The precipitated urea is filtered off with suction, the filtrate is evaporated in vacuo and the residue is taken up in ethyl acetate. The organic phase is washed consecutively with potassium bisulfate, potassium bicarbonate and sodium chloride solutions, dried and evaporated. The residue is chromatographed on silica gel with 1:1 ethyl acetate/cyclohexane.

Yield: 10 g.

$^1$H-NMR data (CDCl$_3$):=4.8–3.8 (m, 2H); 3.8–3.1 (m, 8H); 3.0 (s, 3H); 2.9–1.2 (m, 14H); 1.4 (s, 9H); 1.2 (d, 3H) ppm.

(b) tert.-Butyl S-alanyl-exo-spiro[bicyclo[2.2.2]octane-2,3'-pyrrolidine]-5'-carboxylate 2.0 g of the compound from Example 29a are dissolved in 15 ml of methanol and 1.5 ml of water. The pH is adjusted to 13 with 2N sodium hydroxide solution and the mixture is stirred at room temperature for 2 hours. It is then neutralized with 2N hydrochloric acid, the methanol is evaporated in vacuo, the aqueous phase is extracted with ethyl acetate, and the ethyl acetate solution is washed with water, dried and evaporated. The residue is filtered through silica gel with ethyl acetate as the eluting agent.

Yield: 0.8 g.

$^1$H-NMR data (CDCl$_3$):=4.7–4.2 (m, 1H); 3.9–3.3 (m, 3H); 2.9–1.2 (m, 19H); 1.4 (s, 9H); 1.2 (d, 3H) ppm.

EXAMPLE 30 tert.-Butyl N-(1-S-carboethoxy-3-oxo-3-phenylpropyl)-S-alanyl-exo-spiro[bicyclo[2.2.2]octane-2,3'-pyrrolidine]-5'-carboxylate 5 mmoles of the compound from Example 29b are dissolved together with 5 mmoles of ethyl 3-benzoylacrylate and 5 drops of triethylamine in 50 ml of anhydrous ethanol and the mixture is stirred at 20° to 25° C. for 24 hours. It is then evaporated to dryness and the residue is taken up in ethyl acetate. The solution is now washed with water, dried and evaporated. The mixture of diastereomers is chromatographed on silica gel with ethyl acetate/cyclohexane as the eluting agent. The $^1$H-NMR data agree with the data for the compound from Example 23.

EXAMPLE 31 tert.-Butyl N-(1-S-carboethoxy-3-phenylpropyl)-S-alanylexo-spiro[bicyclo[2.2.2]octane-2,3'-pyrrolidine]-5'-S-carboxylate 5 mmoles of the compound from Example 29b are dissolved in 15 ml of anhydrous ethanol. The pH of the solution is adjusted to 7.0 with ethanolic potassium hydroxide, and 0.7 g of powdered molecular sieve (4 Å) and then 5 mmoles of ethyl 2-keto-4-phenylbutyrate are added. A solution of 0.6 g of sodium cyanoborohydride in 6 ml of anhydrous ethanol is slowly added dropwise. After a reaction time of 20 hours at 20° to 25° C., the solution is filtered and the solvent is distilled off. The residue is taken up in ethyl acetate/water. After evaporating the ethyl acetate phases, the residue is chromatographed on silica gel with 1:4 ethyl acetate/cyclohexane 1:4.

The $^1$H-NMR data agree with the data for the compound from Example 18.

EXAMPLE 32 tert.-Butyl N-(1-S-carboethoxy-3-phenyl-3-oxopropyl)-S-alanyl-exo-spiro[bicyclo[2.2.2]octane-2,3'-pyrrolidine]-5'-S-carboxylate 10 mmoles of acetophenone, 10 mmoles of ethyl glyoxylate and 10 mmoles of the compound from Example 23b in 30 ml of glacial acetic acid are heated at 45° C. for 36 hours. After evaporation in vacuo, the residue is neutralized with sodium carbonate solution and extracted with ethyl acetate. The ethyl acetate phase is evaporated and chromatographed on silica gel with 1:1 ethyl acetate/cyclohexane 1:1 as the eluting agent.

The NMR data agree with the data for the compound from Example 23.

EXAMPLE 33

N-(1-S-Carboethoxy-3-R,S-hydroxy-3-phenylpropyl)-S-alanyl-exo-spiro[bicyclo[2.2.2]octane-2,3'-pyrrolidine]-5'-S-carboxylic acid 0.5 g of the compound from Example 23 are dissolved in 5 ml of aqueous ethanol and 0.1 g of sodium borohydride is added. The mixture is stirred at room temperature for 14 hours. Then ethyl acetate is added, and the ethyl acetate solution is washed with water, dried and evaporated. The crude product is filtered through silica gel with 9:1 ethyl acetate/methanol as the eluting agent.

Yield: 0.3 g.

$^1$H-NMR data (DMSO-d$_6$):=7.3–6.9 (m, 5H); 5.4 (t, 1H); 4.7–4.2 (m, 1H); 3.9–1.3 (m, 20H); 1.3 (d+t, 6H) ppm.

We claim:

1. A compound of the formula I

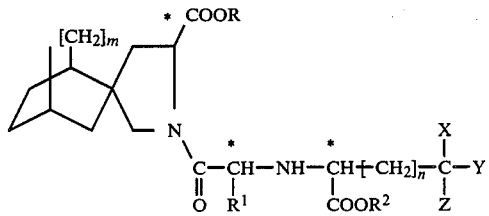

in which
    m denotes 1 or 2,
    n denotes 0 or 1,
    R denotes hydrogen, ($C_1$ to $C_6$)-alkyl or aralkyl having 7 to 9 carbon atoms,
    $R^1$ denotes hydrogen or ($C_1$ to $C_6$)-alkyl which can optionally be substituted by amino, ($C_1$ to $C_6$)-acylamino or benzoylamino, ($C_2$ to $C_6$)-alkenyl, ($C_5$ to $C_9$)-cycloalkyl, ($C_5$ to $C_6$)-cycloalkenyl, ($C_5$ to $C_7$)-cycloalkyl-($C_1$ to $C_4$)-alkyl, ($C_6$ to $C_{12}$)-aryl or partially hydrogenated ($C_6$ to $C_{12}$)-aryl, each of which can be substituted by ($C_1$ to $C_4$)-alkyl, ($C_1$ or $C_2$)-alkoxy or halogen, ($C_6$ to $C_{12}$)-aryl-($C_1$ to $C_4$)-alkyl or ($C_7$ to $C_{13}$)-aroyl-($C_1$ to $C_2$)-alkyl, both of which can be substituted in the aryl radical as defined above, a monocyclic or bicyclic heterocyclic radical having 5 to 7 or 8 to 10 ring atoms respectively, 1 to 2 ring atoms being sulfur or oxygen atoms and/or 1 to 4 ring atoms being nitrogen atoms, or an optionally protected side chain of a naturally occurring α-aminoacid,
    $R^2$ denotes hydrogen, (C1 to C6)-alkyl, (C2 to C6)-alkenyl or ($C_6$ to $C_{12}$)-aryl-($C_1$ to $C_4$)-alkyl,
    Y denotes hydrogen or hydroxyl,
    Z denotes hydrogen or
    Y and Z together denote oxygen and
    X denotes ($C_1$ to $C_6$)-alkyl, ($C_2$ to $C_6$)-alkenyl, ($C_5$ to $C_9$)-cycloalkyl, ($C_6$ to $C_{12}$)-aryl which can be monosubstituted, disubstituted or trisubstituted by ($C_1$ to $C_4$)-alkyl, ($C_1$ to $C_4$)-alkoxy, hydroxy, halogen, nitro, amino, ($C_1$ to $C_4$)-alkylamino, di-($C_1$–$C_4$)-alkylamino and/or methylene-dioxy, or 3-indolyl, and its physiologically acceptable salts.

2. A compound of the formula I as claimed in claim 1, wherein each of the carbon atoms marked with an asterisk has the S configuration.

3. A compound of the formula I as claimed in claim 1, wherein
    m denotes 1 or 2,
    n denotes 1,
    R denotes hydrogen or ($C_1$ to $C_4$)-alkyl,
    $R_1$ denotes hydrogen, ($C_1$ to $C_3$)-alkyl, ($C_2$ or $C_3$)-alkenyl, benzyl, 4-methoxybenzyl, 4-ethoxybenzyl, phenethyl, 4-aminobutyl or benzoylmethyl,
    $R_2$ denotes hydrogen, ($C_1$ to $C_4$)-alkyl or benzyl and
    X denotes cyclohexyl or phenyl which can be monosubstituted or disubstituted, or in the case of methoxy, trisubstituted, by ($C_1$ or $C_2$)-alkyl, ($C_1$ or $C_2$)-alkoxy, hydroxyl, fluorine, chlorine, bromine, amino, ($C_1$ to $C_4$)alkylamino, di-($C_1$ to $C_4$)-alkylamino, nitro and/or methylenedioxy.

4. A compound of the formula I as claimed in claim 1, wherein
    m denotes 1 or 2,
    n denotes 1,
    R denotes hydrogen,
    $R^1$ denotes methyl, 4-methoxybenzyl or 4-ethoxybenzyl and
    $R^2$ denotes hydrogen or ethyl, and the chiral carbon atoms marked with an asterisk (*) have the S configuration.

5. A compound of the formula III

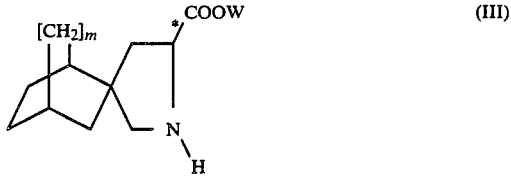

in which m denotes 1 or 2 and W denotes hydrogen or a radical which can be split off with acid or by hydrogenolysis.

6. A pharmaceutical composition comprising an effective amount of a compound or a mixture of compounds as claimed in claim 1 or a pharmaceutically acceptable salt thereof and a pharmaceutically acceptable carrier.

7. A composition as claimed in claim 6 containing a diuretic.

8. A method of treating hypertension by administering an effective amount of a compound as claimed in claim 1 or a pharmaceutically acceptable salt thereof.

* * * * *